United States Patent [19]
Ditzel et al.

[11] Patent Number: 5,877,348
[45] Date of Patent: Mar. 2, 1999

[54] IRIDIUM-CATALYZED CARBONYLATION PROCESS FOR THE PRODUCTION OF ACETIC ACID

[75] Inventors: Evert Jan Ditzel, Howden; John Glenn Sunley, Cottingham; Robert John Watt, Beverly, all of United Kingdom

[73] Assignee: BP Chemicals Limited, London, United Kingdom

[21] Appl. No.: 992,106

[22] Filed: Dec. 17, 1997

[30] Foreign Application Priority Data

Dec. 19, 1996 [GB] United Kingdom .................. 9626429

[51] Int. Cl.$^6$ ............................ C07C 51/12; C07C 51/10
[52] U.S. Cl. ............................................. 562/519; 562/520
[58] Field of Search ...................... 562/519, 520

[56] References Cited

U.S. PATENT DOCUMENTS

| | | | |
|---|---|---|---|
| 5,672,743 | 9/1997 | Garland et al. | 562/519 |
| 5,773,642 | 6/1998 | Denis et al. | 560/232 |

FOREIGN PATENT DOCUMENTS

| | | |
|---|---|---|
| 0 384 652 | 8/1980 | European Pat. Off. . |
| 0 643 034 A1 | 3/1995 | European Pat. Off. . |
| 0 728 727 A1 | 8/1996 | European Pat. Off. . |
| 0 752 406 A1 | 1/1997 | European Pat. Off. . |
| 95/31426 | 11/1995 | WIPO . |

*Primary Examiner*—Gary Geist
*Assistant Examiner*—Rosalynd Keys
*Attorney, Agent, or Firm*—Nixon & Vanderhye

[57] ABSTRACT

A process for the production of acetic acid by carbonylating with carbon monoxide methanol and/or a reactive derivative thereof in a carbonylation reactor containing a liquid reaction composition comprising an iridium carbonylation catalyst, methyl iodide co-catalyst, a finite concentration of water, acetic acid, methyl acetate and at least one promoter wherein the water concentration is at or below that at which the maximum in the graph of carbonylation rate versus water concentration occurs and there is employed in the liquid reaction composition a co-promoter selected from alkali metal iodides, alkaline earth metal iodides, metal complexes capable of generating $I^-$, salts capable of generating $I^-$, and mixtures of two or more thereof.

20 Claims, 5 Drawing Sheets

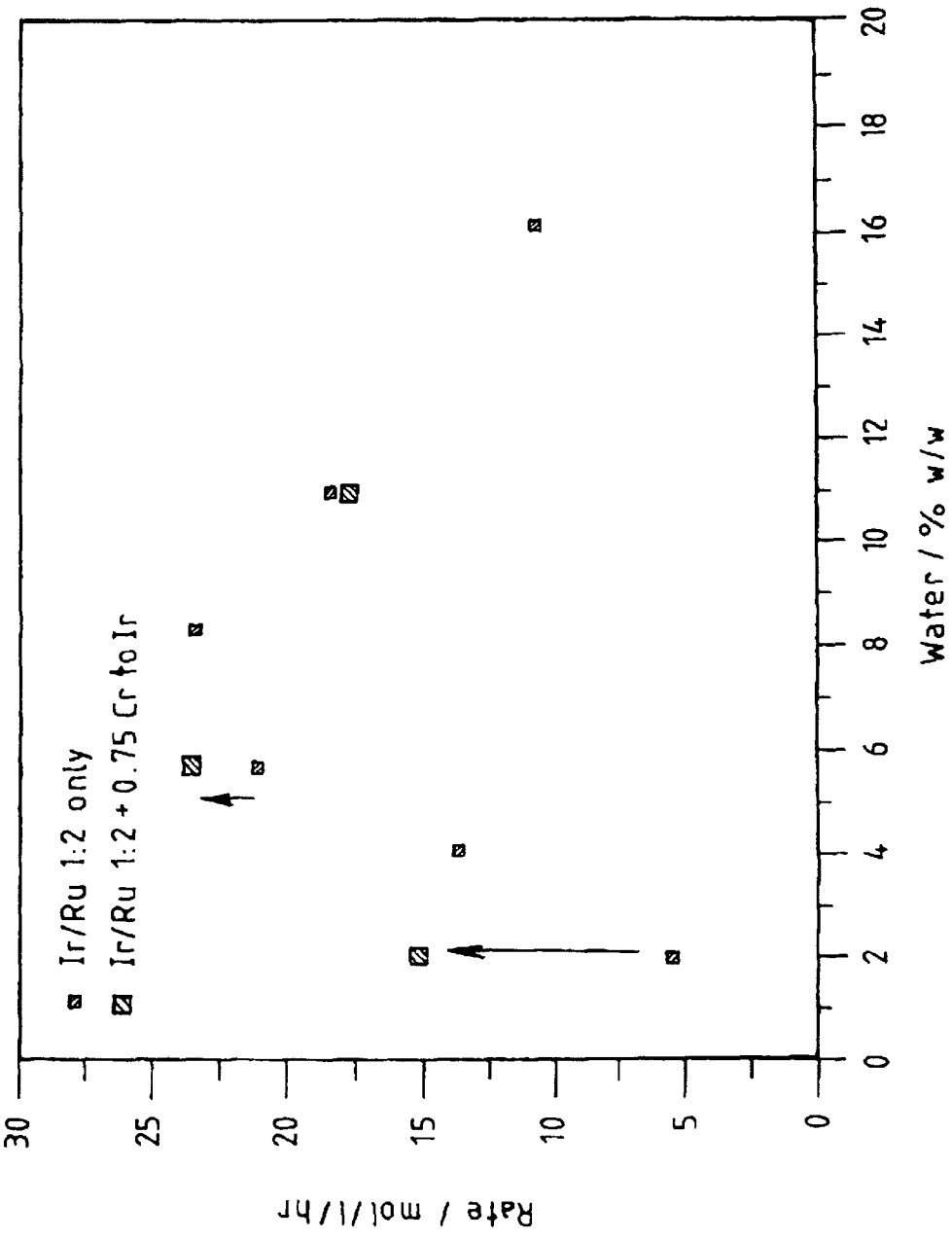
FIG. 1 Batch autoclave; effect of chromium addition on rate for Ir/Ru catalysed methanol carbonylation at 2.1% w/w MeI and 30% MeOAc

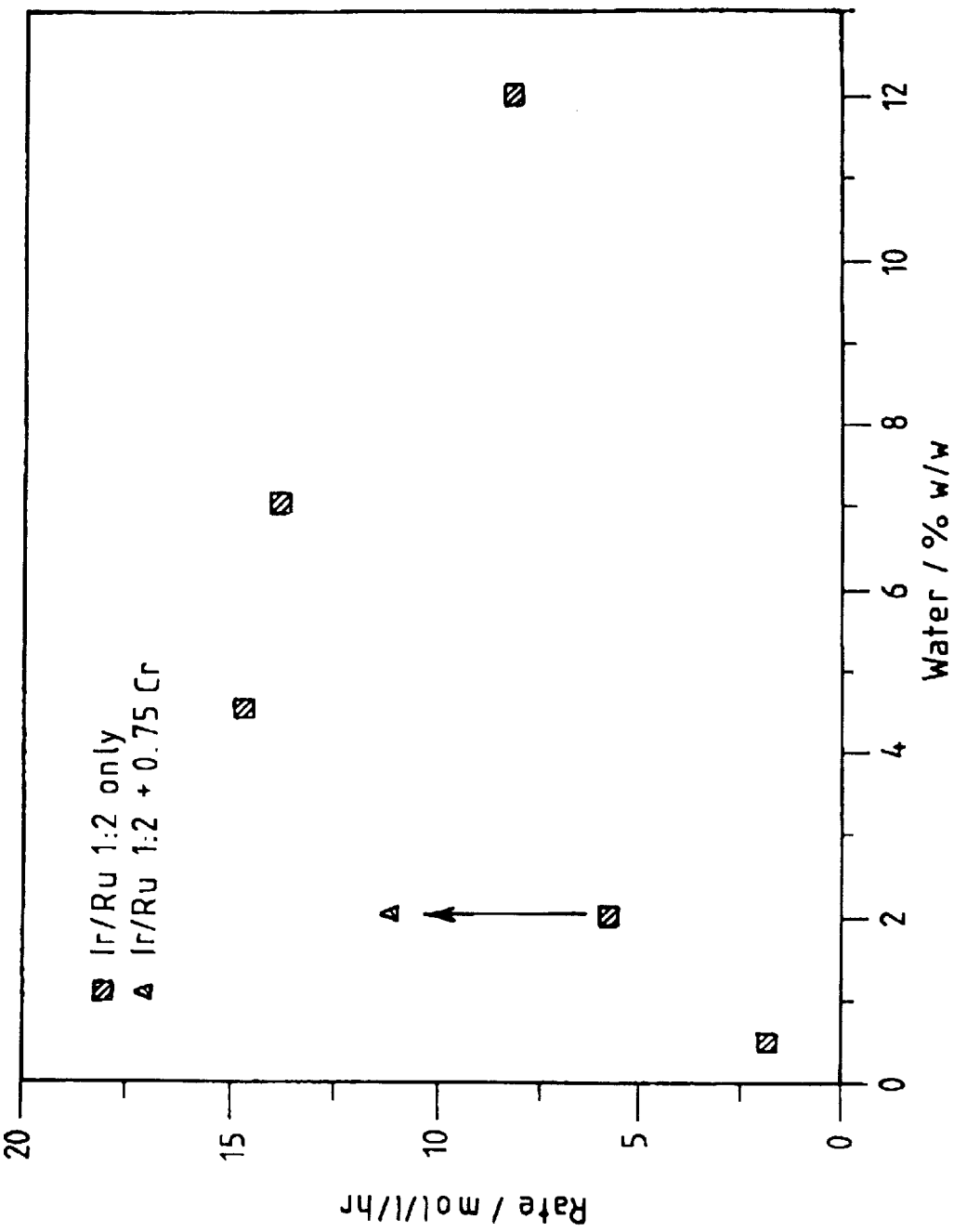
FIG. 2 Batch autoclave; effect of chromium addition on rate for Ir/Ru catalysed methanol carbonylation at 15% MeOAc and 2% MeI

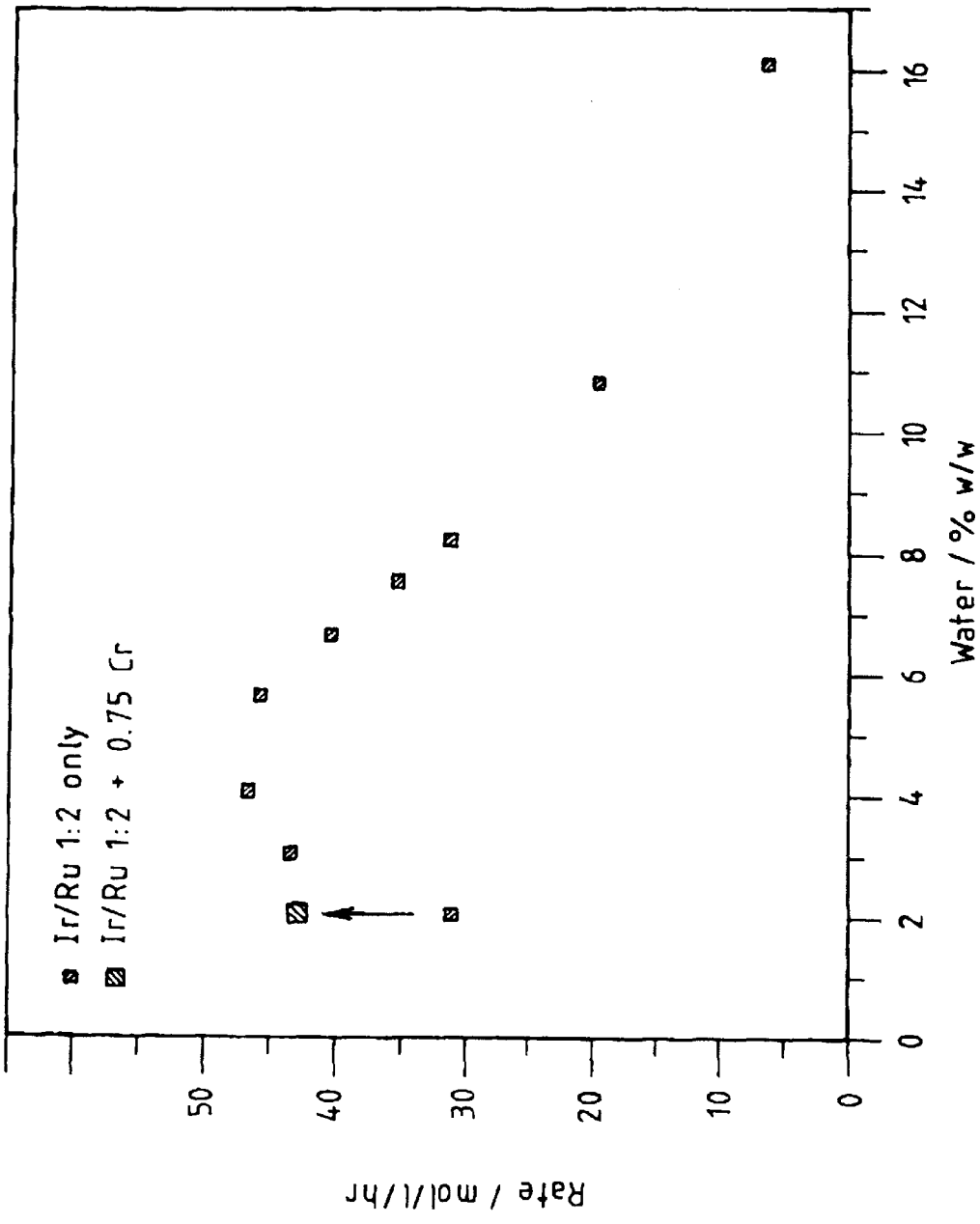
FIG. 3 Batch autoclave; effect of chromium addition on rate for Ir/Ru catalysed methanol carbonylation at 30% MeOAc and 16.9% MeI

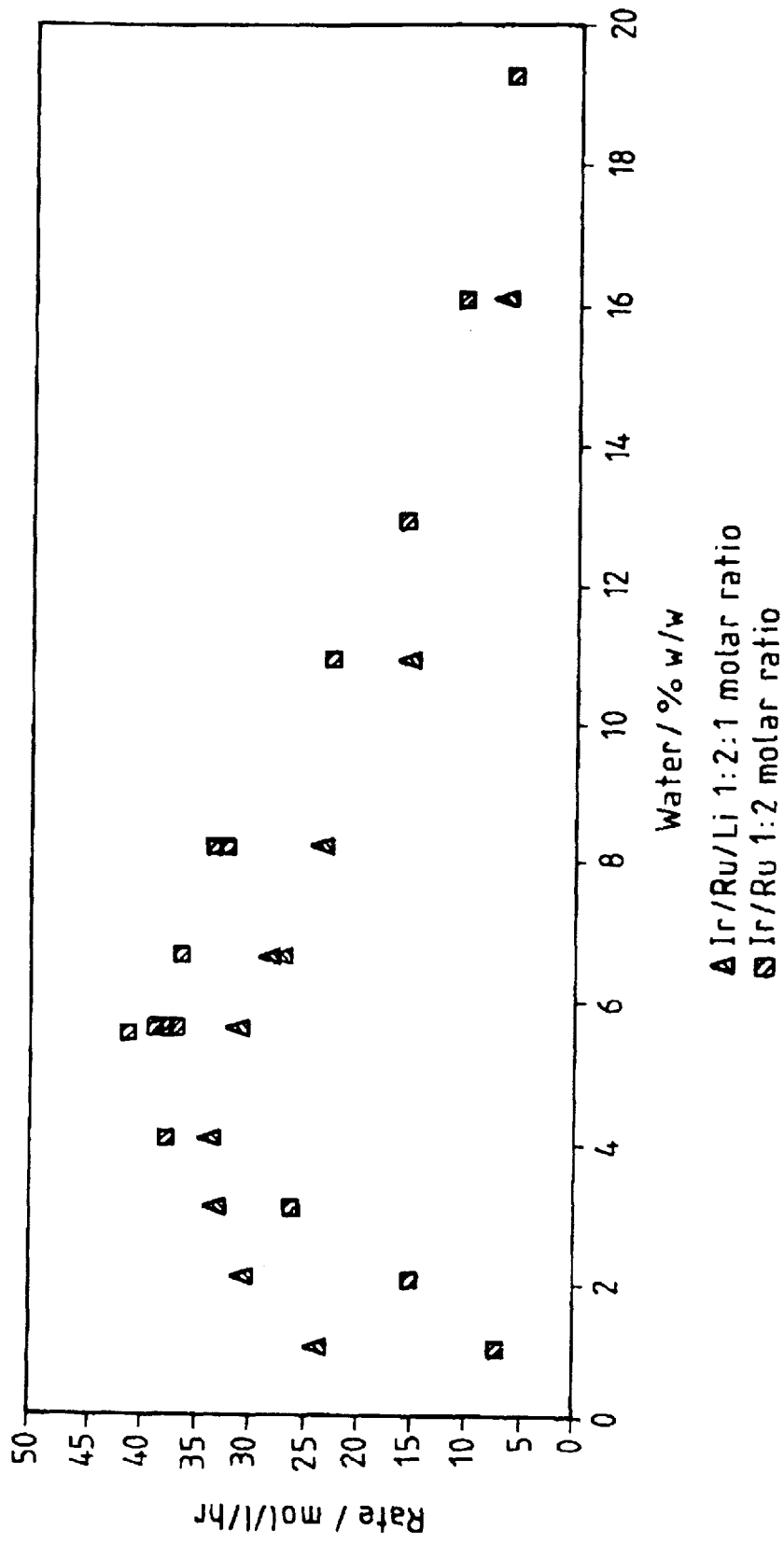
FIG. 4 Batch autoclave; effect of lithium iodide addition on rate for Ir/Ru catalysed methanol carbonylation at 8.4% w/w MeI and 30% w/w MeOAc

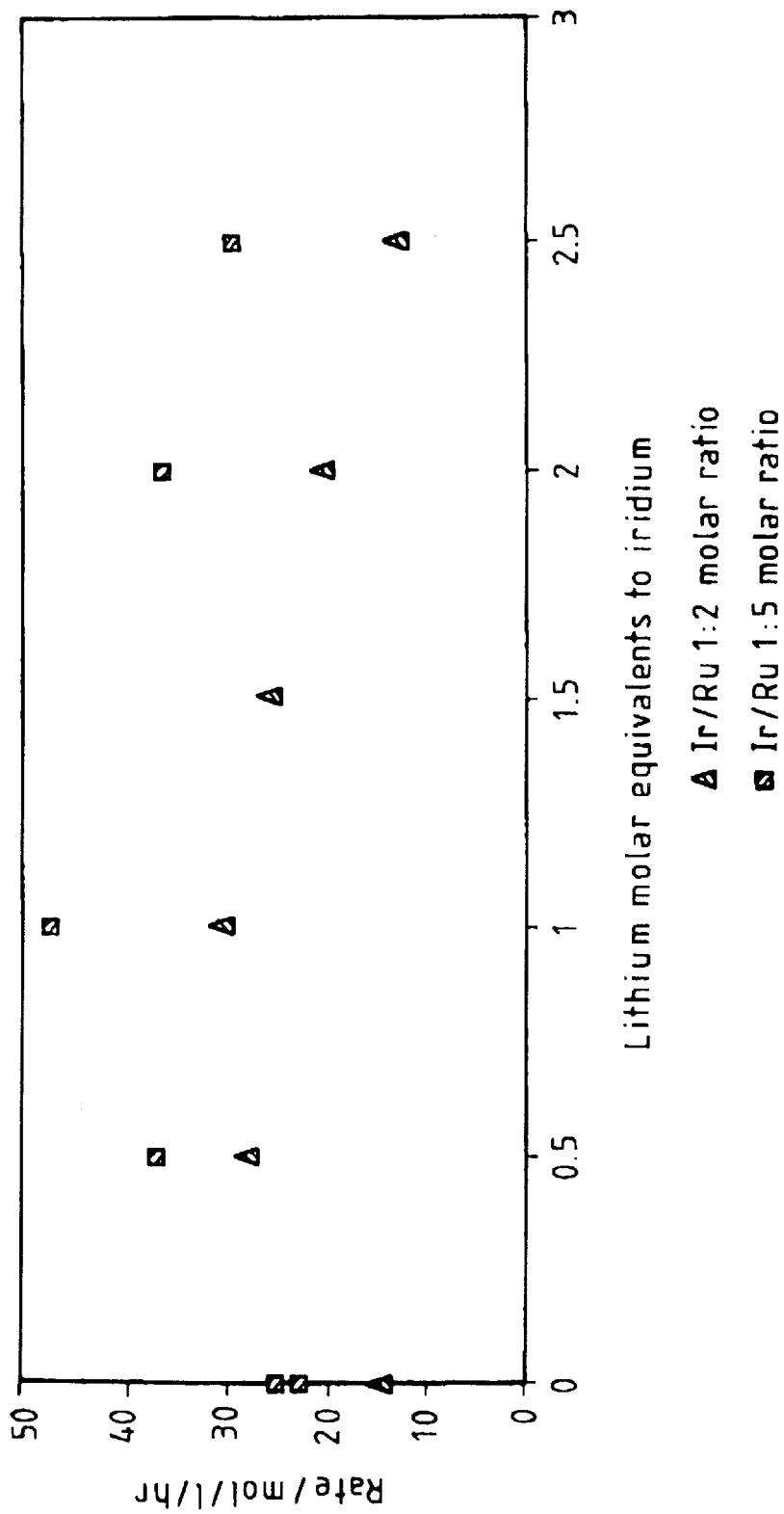
FIG. 5 Batch autoclave: effect of lithium to iridium mole ratio on rate for Ir/Ru catalysed methanol carbonylation at 8.4% w/w MeI, 2% w/w water and 30% w/w MeOAc

IRIDIUM-CATALYZED CARBONYLATION PROCESS FOR THE PRODUCTION OF ACETIC ACID

The present invention relates to a process for the production of acetic acid and in particular to a process for the production of acetic acid by carbonylation in the presence of an iridium catalyst, methyl iodide co-catalyst and a promoter.

Preparation of carboxylic acids by iridium-catalyzed carbonylation processes is known and is described, for example in GB-A-1234121, U.S. Pat. No. 3,772,380, DE-A-1767150, EP-A-0616997, EP-A-0618184, EP-A-0618183, EP-A-0657386 and WO-A-95/31426.

WO-A-95/31426 discloses a process for the production of carboxylic acids or their esters having (n+1) carbon atoms by the liquid phase reaction of carbon monoxide with at least one alcohol having (n) carbon atoms in the presence of a catalytic system based on a compound of iridium and a halogen co-catalyst. The process is characterized by maintaining in the reaction medium water in a volume between greater than 0 and 10%, typically between 0.5 and 8%, preferably between 2 and 8%; the ester corresponding to the carboxylic acid and the alcohol in a volume varying between 2 and 40%; and iodides in soluble form of such a nature that the atomic ratio of the iodides to iridium is between greater than 0 and 10, typically between greater than 0 and 3, preferably between greater than 0 and 1.5. The volume of halogen co-catalyst in the reaction medium is between greater than 0 and 10%; typically between 0.5 and 8%, and preferably between 1 and 6%. Suitable iodides include alkaline earth metal and alkali metal iodides, and specifically lithium iodide. The process of WO-A-95/31426 is otherwise unpromoted.

EP-A-0643034 describes a process for the carbonylation of methanol and/or a reactive derivative thereof in the presence of acetic acid, an iridium catalyst, methyl iodide, at least a finite concentration of water, methyl acetate and a promoter selected from ruthenium and osmium. Batch and continuous experiments are described therein. In the continuous experiments the water concentration is as low as 6.8% by weight.

Our published European Patent Application No. 0752406 filed on 18.04.96 discloses a process for the production of acetic acid comprising (1) continuously feeding methanol and/or a reactive derivative thereof and carbon monoxide to a carbonylation reactor which contains a liquid reaction composition comprising an iridium carbonylation catalyst, methyl iodide co-catalyst, a finite concentration of water, acetic acid, methyl acetate and at least one promoter; (2) contacting the methanol and/or reactive derivative thereof with the carbon monoxide in the liquid reaction composition to produce acetic acid; and (3) recovering acetic acid from the liquid reaction composition characterized in that there is continuously maintained in the liquid reaction composition throughout the course of the reaction (a) water at a concentration of no greater than 6.5% by weight, (b) methyl acetate at a concentration in the range 1 to 35% by weight and (c) methyl iodide at a concentration in the range 4 to 20% by weight.

In the promoted processes of EP-A-0643034 and European Application No. 96302734.7 it is said that ionic contaminants such as, for example, (a) corrosion metals, particularly nickel, iron and chromium and (b) phosphines or nitrogen-containing compounds or ligands which may quaternize in situ should be kept to a minimum in the liquid reaction composition as these will have an adverse effect on the reaction by generating $I^-$ in the liquid reaction composition which has an adverse effect on the reaction rate. Similarly, it is said, contaminants such as alkali metal iodides, for example lithium iodide, should be kept to a minimum.

In WO-A-96/237757 which is directed to the preparation of iridium carboxylates and their use in inter alia carbonylation reactions, the use of promoters not being mentioned, it is stated in contrast to WO-A-95/314326 that alkaline or alkaline earth ions are preferably eliminated, since their presence may have a harmful influence on the kinetics and selectivity of subsequent reactions in which the iridium carboxylate will be used as catalyst.

There remains a need for an improved iridium-catalyzed promoted carbonylation process.

The technical problem is solved by the use in an iridium-catalyzed promoted carbonylation process of a liquid reaction composition defined in terms of water composition and containing a co-promoter selected from alkali metal iodides, alkaline earth iodides, metal complexes capable of generating $I^-$, salts capable of generating $I^-$, and mixtures of two or more thereof Accordingly the present invention provides a process for the production of acetic acid by carbonylating with carbon monoxide methanol and/or a reactive derivative thereof in a carbonylation reactor containing a liquid reaction composition comprising an iridium carbonylation catalyst, methyl iodide co-catalyst, a finite concentration of water, acetic acid, methyl acetate and at least one promoter wherein the water concentration is at or below that at which the maximum in the graph of carbonylation rate versus water concentration occurs and there is employed in the liquid reaction composition a co-promoter selected from alkali metal iodides, alkaline earth metal iodides, metal complexes capable of generating $I^-$, salts capable of generating $I^-$, and mixtures of two or more thereof.

The process of the present invention provides several technical advantages. Thus, the requirement for using an ion exchange resin bed for the purpose of treating the liquid reaction composition to remove corrosion metals, alkali and/or alkaline earth metal contaminants may be reduced.

The increased carbonylation rate at the low water concentration of the present invention may allow operation at a reduced iridium catalyst concentration whilst maintaining the rate of carbonylation. This has benefits of reduced production rate of by-products such as propionic acid.

The rate of production of by-products propionic acid, methane, hydrogen and carbon dioxide may be reduced.

Increased catalyst and promoter stability, particularly at low water concentrations, may also be advantageously achieved.

Water may be formed in situ in the liquid reaction composition, for example, by the esterification reaction between methanol reactant and acetic acid product. Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition.

With reference to the aforesaid published European Application No. 0752406 the rate of the carbonylation reaction is said to increase as the water concentration in the liquid reaction composition is reduced from a concentration of greater than 6.5% by weight, passes through a maximum at a water concentration of no greater than 6.5% by weight and then declines as very low water concentrations are approached. In FIG. 8 of the aforesaid application there is a plot of reaction rate versus water concentration which clearly shows a maximum. The water concentration at which the carbonylation rate is a maximum is said to increase as the concentration of methyl acetate in the liquid reaction composition is increased. It is believed that the water concentration at which the carbonylation rate is a maximum decreases as the concentration of methyl iodide in the liquid reaction composition is increased. For the purpose of the present invention the water concentration in the liquid reaction composition is preferably maintained below 6%, more preferably below 4.5% by weight. Operating at such a low water concentration according to the present invention gives rise to the advantage that recovery of acetic acid from the reaction composition withdrawn from the carbonylation reactor is facilitated because the amount of water which has to be separated from the acetic acid is reduced; separation of water from the acetic acid is an energy-intensive part of the recovery process and reduced water concentration results in reduced processing difficulty and/or costs.

In the process of the present invention, suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. If methyl acetate or dimethyl ether are used, water co-reactant is required to produce acetic acid. At least some of the methanol and/or reactive derivative thereof will be converted to, and hence present as, methyl acetate in the liquid reaction composition by reaction with acetic acid product or solvent. In the process of the present invention the concentration of methyl acetate in the liquid reaction composition is suitably in the range 1 to 70% by weight, preferably 2 to 50% by weight, more preferably 5 to 40% by weight.

In the process of the present invention, the concentration of methyl iodide co-catalyst in the liquid reaction composition is suitably in the range from 1 to 30% by weight, preferably in the range from 1 to 20% by weight.

An advantage of achieving high carbonylation rates at low methyl iodide and water concentrations by the addition of co-promoters according to the present invention may be reduced corrosion, an alternative method of increasing the rate being to increase the methyl iodide concentration which can cause increased corrosion.

In the process of the present invention, the iridium carbonylation catalyst is suitably present in the liquid reaction composition at a concentration in the range 400 to 5000 ppm measured as iridium, preferably in the range 500 to 3000 ppm measured as iridium, more preferably in the range 700 to 3000 ppm measured as iridium. In the process of the present invention, the rate of the carbonylation reaction increases as the concentration of iridium is increased.

The iridium catalyst in the liquid reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution.

In the process of the present invention one or more promoters are present in the reaction composition. Suitable promoters are selected from ruthenium, osmium, tungsten, rhenium, zinc, cadmium, indium, gallium and mercury, and are more preferably selected from ruthenium and osmium. Ruthenium is the most preferred promoter. Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a molar ratio of promoter to iridium of [0.5 to 15]:1, preferably [2 to 10]:1, more preferably [2 to 7.5]:1. A suitable promoter concentration is 400 to 5000 ppm.

The promote may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthermiumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis(benzene) diruthenium(II), dichloro(cycloocta-1,5diene) ruthenium (II) polymer and tris(acetylacetonate)ruthenium (III).

Examples of suitable osmium-containing compounds which may be used as sources or promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, pentachloro-$\mu$-nitrodiosmium and mixed osmium halocarbonyls such as tricarbonyldichloroosmium (II) dimer and other organoosmium complexes.

Examples of suitable tungsten-containing compounds which may be used as sources of promoter include $W(CO)_6$, $WCl_4$, $WCl_6$, $WBr_5$, $WI_2$, or $CH_{12}W(CO)_3$ and any tungsten chloro-bromo- or iodo-carbonyl compound.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.xH_2O$, $[Re(CO)_4I]_2$, $Re(CO)_4I_2]^-H^+$ and $ReCl_5.yH_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$, and $Hg_2Cl_2$.

Examples of suitable zinc-containing compounds which may be used as sources of promoter include $Zn(OAc)_2$, $Zn(OH)_2$, $ZnI_2$, $ZnBr_2$, $ZnCl_2$ and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

There is employed in the liquid reaction composition a co-promoter selected from alkali metal iodides, alkaline earth metal iodides, metal complexes capable of generating $I^-$, salts capable of generating $I^-$, and mixtures of two or more thereof. Suitable alkali metal iodides include lithium iodide. Suitable alkaline earth metal iodides include calcium iodide. Suitable metal complexes capable of generating $I^-$ include complexes of the lanthanide metals, for example, lanthanum and cerium, and nickel, iron, aluminium and chromium, typically $Al(OAc)_2(OH)$ and $Ce(OAc)_3$, hydrate. Salts capable of generating $I^-$ include, for example, acetates which are capable of conversion in-situ to $I^-$ and organic salts, such as quaternary ammonium iodides and phosphonium iodides, which may be added as such. A preferred co-promoter is lithium iodide.

The co-promoter selected from alkali metal iodides, alkaline earth metal iodides, metal complexes capable of generating $I^-$, salts capable of generating $I^-$, and mixtures of two or more thereof, is suitably present in amounts such that it is effective in increasing the carbonylation rate. The amount of such co-promoter introduced to the liquid reaction composition should be selected to take account of the presence of $I^-$ from other sources because it is believed that an excessive amount of $I^-$ in the liquid reaction composition may be detrimental. Using lithium as the co-promoter at a ruthenium to iridium molar ratio of about 2:1, the molar ratio of lithium to iridium may suitably be in the range [0.1 to 2]:1, preferably in the range [0.5 to 1.5]:1. Similar ranges may also be used for the quaternary ammonium and phosphonium iodide co-promoters. At high molar ratios of ruthenium to iridium, e.g. 5:1 or greater, still higher ratios of lithium may be employed and a promotional effect obtained. Typically, for example when using lithium as the co-promoter when the ruthenium to iridium molar ratio is about [2:1] the molar ratio lithium to iridium is suitably in the range [0.5 to 1.5]:1. Uncertainty regarding, amongst other factors, the oxidation state of the metal centre in the reaction solution render it difficult to specify suitable concentration ranges for other sources of iodide ions. Typically, however for divalent and trivalent metal salts a suitable co-promoter range may be [0.1 to 1]:1 molar equivalents to iridium with a promoter ratio of [2 to 10]:1 molar equivalents to iridium.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than 1 bar partial pressure, more preferably less than 0.5 bar and yet more preferably less than 0.3 bar. The partial pressure of carbon monoxide in the reactor is in the range greater than 0 to 40 bar, typically from 4 to 30 bar.

The total pressure of the carbonylation reaction is suitably in the range 10 to 200 barg, preferably 15 to 100 barg, more preferably 15 to 50 barg. The temperature of the carbonylation reaction is suitably in the range 100° to 300° C., preferably in the range 150° to 220° C.

The process of the present invention may be performed as a batch or as a continuous process, preferably as a continuous process.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as iridium catalyst, methyl iodide co-catalyst, promoter, methyl acetate, unreacted methanol and/or reactive derivative thereof, water and acetic acid solvent which may be recycled to the reactor to maintain their concentrations in the liquid reaction composition. To maintain stability of the iridium catalyst during the acetic acid product recovery stage, water in process streams containing iridium carbonylation catalyst for recycle to the carbonylation reactor should be maintained at a concentration of at least 0.5% by weight.

BRIEF DESCRIPTION OF DRAWINGS

The invention will now be illustrated by way of example only and with reference to the following examples and FIGS. 1 to 5 which represent in graph form, the carbonylation rate at different water concentrations for ruthenium promoted reactions at different methyl iodide and methyl acetate concentrations.

GENERAL DESCRIPTION OF THE CARBONYLATION EXPERIMENTS

All experiments were performed using a 300 ml zirconium autoclave equipped with a magnetically driven stirrer with gas dispersion impellers, liquid catalyst injection facility and cooling coils. A gas supply to the autoclave was provided from a ballast vessel, feed gas being provided to maintain the autoclave at a constant pressure. The rate of gas uptake at a certain point in a reaction run was used to calculate the carbonylation rate, as number of moles of reactant consumed per liter of cold degassed reactor composition per hour {mol/l/hr}, at a particular reactor composition (reactor composition based on a cold degassed volume).

The methyl acetate concentration was calculated during the course of the reaction from the starting composition, assuming that one mole of methyl acetate is consumed for every mole of carbon monoxide that is consumed. No allowance was made for organic components in the autoclave headspace.

For each batch carbonylation experiment the catalyst, $H_2IrCl_6$, dissolved in a portion of the acetic acid / water liquid reactor charge, was charged to the liquid injection facility. The reactor was then pressure tested with nitrogen, vented via a gas sampling system, and flushed with carbon monoxide several times (3×3–10 barg). If a promoter or additive was used this was placed in the autoclave and covered with a portion of the acetic acid charge (ca. 10 g) prior to the pressure test. The remaining liquid components of the reaction composition were charged to the autoclave via a liquid addition port. The autoclave was then optionally pressurized with 5 barg of carbon monoxide and slowly vented. The autoclave was then pressurized with carbon monoxide (typically 6 barg) and heated with stirring (1500 rpm) to reaction temperature, 190° C. The total pressure was then raised to approximately 3 barg below the desired operating pressure by feeding forward carbon monoxide from the ballast vessel. Once stable at temperature (about 15 minutes) the catalyst was injected using an over pressure of carbon monoxide. The catalyst injection facility has an efficiency of >90%. The reactor pressure was maintained at a constant value (±0.5 barg) by feeding gas from the ballast vessel throughout the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) control system. In addition, excess heat of reaction was removed by means of cooling coils. Each run was conducted until the gas uptake had ceased, i.e. until less than 0.1 bar per minute of gas was consumed from the ballast vessel. The ballast vessel was then isolated and the reactor crash cooled by use of the cooling coils. $H_2IrCl_6$ (aqueous solution) was supplied by Johnson Matthey. The acetic acid was obtained from carbonylation of a mixed methanol/methyl acetate feedstock and contained very low amounts of propionic acid and its precursors. Methyl acetate, water and methyl iodide were supplied by Aldrich. $[Ru(CO)_4I_2]$ was synthesised from $[Ru_3(CO)_{12}]$ (STREM Chemicals) and iodine (Aldrich). Chromium (III) iodide, gallium (III) iodide, indium (III) iodide and iron (II) iodide were supplied by STREM Chemicals. Charge compositions are given in Table 1.

EXAMPLES 1 to 13 and EXPERIMENTS A to J

The general procedure described hereinabove was employed. The charge compositions are given in Table 1.

Experiments A to J are not according to the present invention for the reason that either no promoter was employed or no co-promoter was employed or the water concentration was above that at which the maximum in the graph of carbonylation rate versus water concentration occurs.

Experiments D and Examples 1 and 2 in Table 2 demonstrate the effect of the addition of chromium, added as chromium (III) iodide, on carbonylation activity using a ruthenium promoted iridium catalyst (ca. two molar equivalents of ruthenium to iridium) at 190° C. and 28 barg total pressure. Rate data, at various methyl acetate (MeOAc) and water concentrations, are given in Table 2.

For purpose of comparison, further experiments, at 190° C. and 28 barg total pressure, were performed using a ruthenium promoted iridium catalyst (ca. two molar equivalents of ruthenium to iridium) to determine the relationship between the carbonylation rate and water concentration, at 30% w/w MeOAc and 2.1% methyl iodide (MeI), and at 15% w/w MeOAc and 2.0% w/w MeI. Data from these additional experiments is displayed graphically in FIGS. 1 & 2 along with data from Experiments A to D and Examples 1 and 2. The rate data in Table 2 and FIGS. 1 & 2 illustrate the beneficial effect of adding chromium, added as chromium (III) iodide, 0.75 molar equivalents to iridium, to a ruthenium promoted reaction when the carbonylation rate is declining with decreasing water concentration. For example, at 30% w/w MeOAc, 2.1% w/w MeI and 2.0% w/w water addition of chromium increases the carbonylation rate from 5.4 to 15.2 mol/l/hr.

Comparison of Example 3 with Experiment B demonstrates the beneficial effect on the carbonylation rate of adding iron, added as iron (II) iodide, 0.75 molar equivalents to iridium, to a ruthenium promoted reaction at 30% w/w MeOAc, 2.1% w/w MeI and 2.0% w/w water. Addition of iron under these conditions increases the carbonylation rate from 5.4 to 10.2 mol/l hr.

Comparison of Experiment E and Example 4, Table 3, demonstrates the beneficial effect on the carbonylation rate of adding chromium, added as chromium (III) iodide, 0.75 molar equivalents to iridium, to a ruthenium promoted reaction at a relatively high MeI concentration of 16.9% w/w at water concentration of 2.0% w/w at 30% w/w MeOAc.

For purpose of comparison further experiments, at 190° C. and 28 barg total pressure, were performed using a ruthenium promoted iridium catalyst to determine the relationship between the carbonylation rate and water concentration, at 30% w/w MeOAc and 16.9% MeI. Rate data from these additional experiments is displayed graphically in FIG. 3 along with data from Experiment E and Example 4. FIG. 3 illustrates the beneficial effect of adding chromium, 0.75 molar equivalents to iridium, to a ruthenium promoted reaction when the carbonylation rate is declining with decreasing water concentration at 16.9% w/w MeI and 30% w/w MeOAc, the carbonylation rate being increased from 31.1 to 42.9 mol/l/hr.

Comparison of Example 5 with Experiment H, Table 4, demonstrates the beneficial effect on the carbonylation rate of adding lithium, added as lithium iodide, 1 molar equivalent to iridium, to a ruthenium promoted reaction at 30% w/w methyl acetate, 8.4% w/w methyl iodide and 2.0% w/w water. Addition of lithium iodide under these conditions increases the carbonylation rate from 15.1 to 30.8 mol/l/hr. Furthermore comparison of Experiment F with Experiment G shows that adding lithium iodide to an unpromoted iridium catalysed reaction has a detrimental effect on the carbonylation rate under the same conditions. Rate data from Experiments F to H and Example 5 are summarized in the Table below.

| Experiment/ Example | Catalyst System | Water (% w/w) | Rate/mole/hr at 30% MeOAc |
|---|---|---|---|
| F | Ir only | 2.0 | 12.1 |
| G | Ir/Li 1:1 | 2.0 | 6.3 |
| H | Ir/Ru 1:2 | 2.0 | 15.1 |
| 5 | Ir/Ru/Li 1:2:1 | 2.0 | 30.8 |

For the purpose of comparison further experiments, at 190° C. and 28 barg total pressure, were performed using a ruthenium promoted iridium catalyst, in both the absence and presence of lithium iodide, to determine the relationship between the carbonylation rate and water concentration, at 30% w/w methyl acetate and 8.4% w/w methyl iodide. Rate data from these additional experiments is displayed graphically in FIG. 4, which illustrates the beneficial effect of adding lithium iodide to a ruthenium promoted reaction when the rate is declining with decreasing water concentration. The reaction rate for these experiments was also determined at lower methyl acetate concentrations, for example at 15% w/w methyl acetate. Comparison of Experiment 1 with Example 6 in the table below demonstrates the beneficial effect of adding lithium, added as lithium iodide, at 15% w/w methyl acetate, 0.5% w/w water and 8% w/w methyl iodide.

| Experiment/ Example | Catalyst System | Water/ % w/w | Rate/mol/hr @ 15% MeOAc |
|---|---|---|---|
| 1 | Ir/Ru 1:2 | 0.5 | 6.5 |
| 6 | Tr/Ru/Li 1:2:1 | 0.5 | 12.2 |

FIG. 5 illustrates the effect on carbonylation rate of the molar ratio of lithium to iridium for a series of ruthenium promoted reactions at 30% w/w methyl acetate, 2% w/w water and 8.4% w/w methyl iodide. Under these conditions it can be seen that the optimum molar ratio of lithium to iridium lies between 0.5:1 and 1.5:1 at both ruthenium to iridium molar ratios of 2:1 and 5:1.

Experiment H was repeated using various promoter and additive combinations, Examples 7 to 14 and Experiments I and J, Table 5. Examples 7 to 11, 13 and 14 show that various additives, which are all sources of ionic iodide, are effective as co-promoters under the conditions of the present invention. Examples 8 and 11, with aluminium acetate and cerium acetate respectively, demonstrate that the co-promoters may be added in their acetate form. Comparison of Experiment J with Example 12 demonstrates that lithium, added as lithium iodide, 1 molar equivalent to iridium, is a co-promoter for a gallium promoted iridium catalyst under the conditions of the present invention.

TABLE 1

Charge compositions for ruthenium promoted reactions in a 300 ml zirconium batch autoclave.

| Experiment/ Example | Run No. | MeOAc/g | AcOH/g | MeI/g | Water/g | $H_2IrCl_6$/g a | $Ru(CO)_4I_2$/g | Additive | Amount/g |
|---|---|---|---|---|---|---|---|---|---|
| A | 747 | 60.04 | 71.89 | 4.16 | 11.91 | 0.635 | 1.46 | — | — |
| 1 | 802 | 60.08 | 71.33 | 4.16 | 11.92 | 0.636 | 1.46 | CrI3 | 0.506 |
| B | 753 | 60.04 | 77.35 | 4.16 | 6.42 | 0.635 | 1.46 | — | — |
| 2 | 805 | 60.04 | 76.84 | 4.16 | 6.40 | 0.636 | 1.46 | CrI3 | 0.506 |
| 3 | 806 | 60.00 | 76.98 | 4.16 | 6.40 | 0.636 | 1.46 | FeI2 | 0.362 |
| C | 741 | 60.10 | 63.68 | 4.16 | 20.15 | 0.639 | 1.46 | — | — |
| D | 804 | 60.05 | 63.22 | 4.16 | 20.11 | 0.636 | 1.46 | CrI3 | 0.506 |
| E | 699 | 60.04 | 54.46 | 27.05 | 6.39 | 0.642 | 1.46 | — | — |
| 4 | 803 | 60.05 | 53.96 | 27.03 | 6.41 | 0.636 | 1.46 | CrI3 | 0.506 |
| F | 642 | 60.02 | 68.99 | 13.96 | 6.46 | 0.642 | — | — | — |
| G | 817 | 60.0 | 68.80 | 13.96 | 6.41 | 0.637 | — | LiI | 0.209 |
| H | 651 | 60.07 | 67.71 | 13.94 | 6.41 | 0.642 | 1.46 | — | — |
| 5 | 810 | 59.99 | 67.32 | 13.96 | 6.42 | 0.637 | 1.46 | LiI | 0.209 | a) Weight expressed as pure $H_2IrCl_6$.

TABLE 2

Rate data for iridium/ruthenium catalyzed reactions in 300 ml autoclave.[a]

| Experiment/ Example | Water/% w/w | Rate/ mol/l/hr @ 30% MeOAc | Water/% w/w | Rate/ mol/l/hr @ 25% MeOAc | Water/% w/w | Rate/ mol/l/hr @ 20% MeOAc | Water/% w/w | Rate/ mol/l/hr @ 15% MeOAc | Water/% w/w | Rate/ mol/l/hr @ 10% MeOAc |
|---|---|---|---|---|---|---|---|---|---|---|
| A (747) | 5.6 | 21.2 | 4.4 | 16.6 | 3.2 | 11.4 | 2.0 | 5.7 | 0.8 | 3.0 |
| 1 (802) | 5.6 | 23.6 | 4.4 | 19.6 | 3.2 | 15.6 | 2.0 | 11.1 | 0.8 | 6.4 |
| B (753) | 2.0 | 5.4 | 0.9 | 2.7 | — | — | — | — | — | — |
| 2 (805) | 2.0 | 15.2 | 0.9 | 10.1 | — | — | — | — | — | — |
| 3 (806) | 2.0 | 10.2 | 0.9 | 6.3 | — | — | — | — | — | — |
| C (741) | 10.9 | 18.4 | 9.6 | 17.1 | 8.3 | 15.7 | 7.0 | 13.8 | 5.8 | 11.2 |
| D (804) | 10.9 | 17.7 | 9.6 | 16.8 | 8.3 | 15.6 | 7.0 | 13.9 | 5.7 | 11.2 |

| Experiment/ Example | Water/% w/w | Rate/mol/l/hr @ 7.5% MeOAc | Water/% w/w | Rate/mol/l/hr @ 5% MeOAc |
|---|---|---|---|---|
| C (741) | 5.1 | 9.2 | 4.5 | 6.7 |
| D (804) | 5.1 | 9.2 | 4.5 | 5.9 | a) All reactions at 28 barg total pressure and 190° C. with a stirrer speed of 1500 rpm.
ca. 2.1% MeI at 30% MeOAc
ca. 2.0% MeI at 15% MeOAc
MeI concentration is adjusted slightly downwards based upon the approximation that each mole of iridium can consume a maximum of 4 moles of methyl iodide to give $[Ir(CO)_2I_4]^-$.

TABLE 3

Rate data for iridium/ruthenium catalyzed reactions in 300 ml autoclave.[a]

| Experiment | Water/% w/w | Rate/mol/l/hr @ 30% MeOAc | Water/% w/w | Rate/mol/l/hr @ 25% MeOAc |
|---|---|---|---|---|
| E (699) | 2.0 | 31.1 | 0.9 | 17.4 |
| 4 (803) | 2.0 | 42.9 | 0.9 | 26.9 | a) All reactions at 28 barg total pressure and 190° C. with a stirrer speed of 1500 rpm.
ca. 16.9% MeI at 30% MeOAc.
MeI concentration is adjusted slightly downwards based upon the approximation that each mole of iridium can consume a maximum of 4 moles of methyl iodide to give $[Ir(CO)_2I_4]^-$.

TABLE 4

Rate data for iridium catalysed reactions in a 300 ml zirconium batch autoclave.[a]

| Experiment/ Example | Catalyst System | Water % w/w | Rate/mol/l/hr @ 30% MeOAc | Water % w/w | Rate/mol/l/hr @ 25% MeOAc |
|---|---|---|---|---|---|
| F (642) | Ir only | 2.1 | 12.1 | 0.9 | 5.9 |
| G (817) | Ir/Li 1:1 | 2.0 | 6.3 | 0.9 | 4.4 |
| H (651) | Ir/Ru 1:2 | 2.0 | 15.1 | 0.9 | 7.5 |
| 5 (810) | Ir/Ru/Li 1:2:1 | 2.0 | 30.8 | 0.9 | 21.0 | a) All reactions at 28 barg total pressure and 190° C. with a stirrer speed of 1500 rpm.
Ca 8.4% w/w MeI at 30% w/w MeOAc.
MeI concentration is adjusted slightly downwards based upon the approximation that each mole of iridium can consume a maximum of 4 moles of methyl iodide to give $[Ir(CO)_2I_4]^-$.

TABLE 5

Effect of various additives on rate for iridium catalyzed methanol carbonylation at 30% w/w methyl acetate and ca. 2% w/w water using various promoters.[a]

| Experiment/ Example | Promotoer | Promoter: Ir/molar ratio | Additive | Additive: Ir/molar ratio | Rate/mol/l/hr @ 30% MeOAc |
|---|---|---|---|---|---|
| H (651) | $Ru(CO)_4I_2$ | 2:1 | None | — | 15.1 |
| 7 (852) | $Ru(CO)_4I_2$ | 2:1 | N—Me-4-$^t$Bu-pyridinium iodide | 1:1 | 27.5 |
| 8 (853) | $Ru(CO)_4I_2$ | 2:1 | $Al(OAc)_2(OH)$ | 0.5:1 | 34.1 |
| 9 (854) | $Ru(CO)_4I_2$ | 2:1 | $LaI_3$ | 0.5:1 | 29.3 |
| 10 (856) | $Ru(CO)_4I_2$ | 2:1 | $[PBu_3Me][I]$ | 1:1 | 26.7 |
| 11 (858) | $Ru(CO)_4I_2$ | 2:1 | $Ce(OAc)_3$.hydrate | 0.5:1 | 32.6 |
| J (851) | $GaI_3$ | 2:1 | — | — | 14.0 |
| 12 (855) | $GaI_3$ | 2:1 | LiI | 1:1 | 17.6 |
| 13 (851) | $InI_3$ | 2:1 | LiI | 1:1 | 20.6 |
| 14 (917) | $Ru(CO)_4I_2$ | 2:1 | $CaI_2$ | 0.5:1 | 28.3 | a) All reactions at 28 barg total pressure and 190° C. with a stirrer speed of 1500 rpm.
Ca 8.4% w/w MeI at 30% MeOAc w/w.
MeI concentration is adjusted slightly downwards based upon the approximation that each mole of iridium can consume a maximum of 4 moles of methyl iodide to give $[Ir(CO)_2I_4]^-$.

We claim:

1. A process for the production of acetic acid by carbonylating with carbon monoxide methanol and/or a reactive derivative thereof in a carbonylation reactor containing a liquid reaction composition comprising an iridium carbonylation catalyst, methyl iodide co-catalyst, a finite concentration of water, acetic acid, methyl acetate and at least one promoter wherein the water concentration is at or below that at which the maximum in the graph of carbonylation rate versus water concentration occurs and there is employed in the liquid reaction composition a co-promoter selected from alkali metal iodides, alkaline earth metal iodides, metal complexes capable of generating $I^-$, salts capable of generating $I^-$, and mixtures of two or more thereof.

2. A process according to claim 1 wherein the water concentration in the liquid reaction composition is below 6% by weight.

3. A process according to claim 2 wherein the water concentration in the liquid reaction composition is below 4.5% by weight.

4. A process according to claim 1 wherein methanol and/or methyl acetate are carbonylated.

5. A process according to claim 1 wherein the concentration of methyl acetate in the liquid reaction composition is in the range 5 to 40% by weight.

6. A process according to claim 1 wherein the concentration of methyl iodide co-catalyst in the liquid reaction composition is in the range from 1 to 20% by weight.

7. A process according to claim 1 wherein iridium carbonylation catalyst is present in the liquid reaction composition at a concentration in the range 500 to 3000 ppm measured as iridium.

8. A process according to claim 1 wherein at least one promoter is selected from ruthenium, osmium, tungsten, rhenium, zinc, cadmium, indium, gallium and mercury.

9. A process according to claim 8 wherein the promoter is ruthenium.

10. A process according to claim 1 wherein the promoter is present in the liquid reaction composition at a molar ratio of promoter:iridium of 0.5:1 to 15:1.

11. A process according to claim 1 wherein the co-promoter is an alkali metal iodide.

12. A process according to claim 11 wherein the alkali metal iodide is lithium iodide.

13. A process according to claim 1 wherein the co-promoter is an alkaline earth metal iodide.

14. A process according to claim 1 wherein the co-promoter is a metal complex capable of generating $I^-$.

15. A process according to claim 14 wherein the metal is lanthanum, cerium, aluminium, nickel, iron or chromium.

16. A process according to claim 15 wherein the metals are in the form of their iodides.

17. A process according to claim 1 wherein the co-promoter is a salt capable of generating $I^-$.

18. A process according to claim 17 wherein the salt is a quaternary ammonium or phosphonium iodide.

19. A process according to claim 1 wherein the co-promoter is lithium, the ruthenium to iridium molar ratio is about 2:1 and the molar ratio of lithium to iridium is in the range 0.5:1 to 1.5:1.

20. A process according to claim 1 wherein the carbonylation reaction temperature is in the range 150° to 220° C. and the total pressure is in the range 15 to 100 barg.

* * * * *